United States Patent [19]

van der Veek

[11] 4,171,351
[45] Oct. 16, 1979

[54] TELLURYL COMPOUNDS, THEIR PREPARATION AND USE

[75] Inventor: Augustinus P. M. van der Veek, Voorschoten, Netherlands

[73] Assignee: Nederlandse Organisatie Voor Toegepast-Natuurwetenschappelijk Onderzoek ten Behoeve Van Nijverheid, Handel En Verkeer, The Hague, Netherlands

[21] Appl. No.: 799,526

[22] Filed: May 23, 1977

[30] Foreign Application Priority Data

May 28, 1976 [NL] Netherlands ........................ 7605739

[51] Int. Cl.$^2$ ........................ A61K 43/00; C07J 7/00; C07J 9/00
[52] U.S. Cl. ..................................... 424/1; 260/397.2; 260/397.3; 260/397.4; 260/397.45
[58] Field of Search ........ Machine Searched Steroids; 260/397.2, 397.45, 397.3, 397.4; 424/1

[56] References Cited

U.S. PATENT DOCUMENTS

| 3,952,030 | 4/1976 | Chambers et al. | 260/397.2 |
| 4,024,234 | 5/1977 | Monks et al. | 260/397.2 |
| 4,041,145 | 8/1977 | van der Veek | 260/397.2 |

Primary Examiner—Ethel G. Love
Attorney, Agent, or Firm—Hammond & Littell

[57] ABSTRACT

The preparation of novel organic telluryl derivatives, which may comprise radioactive telluryl isotopes, and more particularly, of derivatives of steroids having in the $CH_3$-radical at position 19 a branched alkyl-Te-radical as substituent (e.g. the neopentyl-Te-group).

The derivatives obtained are suitable for diagnostic purposes; the radioactively labelled ones can be used in organ scanning as well as for radio immunologic determinations in body fluids.

18 Claims, 5 Drawing Figures

TELLURYL COMPOUNDS, THEIR PREPARATION AND USE

BACKGROUND OF THE INVENTION

The invention relates to novel telluryl compounds, methods for preparing them and to novel intermediate products that can be applied for these methods, as well as to diagnostic preparations based on the novel compounds.

More in particular, but not exclusively, the invention relates to novel telluryl derivatives of steroids and, more in particular, to such compounds labelled with radioactive tellurium.

Preparations on the latter compounds may be applied for diagnostic investigation into abnormalities of internal organs as well as the radio-immunologic determination of the steroid content in bodily fluids such as blood or urine. The non-radioactively labelled novel telluryl compounds according to the invention can also be used for the determination of the steroid-level in bodily fluids.

For the diagnostic investigation into abnormalities of internal organs according to the "scintigraphic" method use has been made for several years, i.a. of steroids labelled with iodine-isotopes, such as cholesterol for the scanning of the adrenals.

Since the use of radioactively labelled iodine derivatives, such as $^{131}$I-iodine-cholesterol, for this purpose leads to undesirable irradiation load of the body, more in particular of the thyroid gland, mainly as a result of the $\beta$-irradiation produced by these derivatives, it has been proposed to use compounds labelled with radioactive selenium for this purpose- see for selenium-cholesterol Netherlands Patent Application 75 02022 laid-open for public inspection (corresponding to UK patent application No. 7808/74).

Though because of the absence of $\beta$-irradiation, the irradiation specificity of compounds labelled with radioactive selenium is more favourable than that from the derivatives that are suitable for the above purpose and that are labelled with radioactive iodine, the former labelled selenium compounds have also obvious drawbacks yet. In particular the proposed $^{75}$Se isotope yields a very complicated irradiation picture because it emits $\gamma$-irradiations of very different energies, which upon scanning adversely affect the dissolution power. As a result it is not easy to obtain, with the dose of radioactive selenium maximally acceptable from a radiobiological point of view, an adequate picture of the organ to be "scanned," so that the diagnosis is seriously hampered.

SUMMARY OF THE INVENTION

The object of the invention is to solve the existing disadvantages by utilizing chemically stable compounds labelled with radioactive tellurium for the scanning of internal organs.

For the radioactive tellurium, in this case the $^{123m}$Te isotope, mainly emits $\gamma$-irradiation of one certain energy, i.e. of 159 keV, as a result of which with a minimum dose of a compound labelled with radioactive tellurium an extremely sharp picture can be obtained so that a quick and adequate diagnosis is allowed.

For completeness' sake it ought to be remarked that the idea of using radioactive tellurium derivatives for this purpose was also casually suggested in the pending Netherlands patent application No. 74 15526 (U.S. patent application Ser. No. 636,099 now U.S. Pat. No. 4,041,145) of the same inventor, but that the only telluryl derivative, the 19-methyl telluryl cholesteryl acetate, described in it, on further examination has been found unsuitable for said purpose because of its chemical instability.

The Applicant now surprisingly has found that telluryl derivatives that instead of with a methyl group are provided with a highly branched alkyl group show such a chemical stability that they are particularly appropriate for organ scanning. Thus the invention in particular relates to novel, chemically stable telluryl derivatives and specifically to novel, chemically stable telluryl derivatives of steroids, including the corresponding radioactively labelled derivatives.

The radioactive telluryl isotope can be introduced in the molecule at various positions, but preferably at the 19-position of the steroid because this position is very favourable from a structural point of view; for then the characteristic functional groups of the molecule are hardly affected. This is especially of importance upon application of the compounds according to the invention for the determination of the steroid-level because it is a question of a competitive compound of labelled steroid and natural steroid with an antibody. In the process, every deviation in the behavior of the labelled steroid in respect of the natural steroid may have a disturbing effect. Such deviations are reduced to a minimum upon substituting in the 19-position, so that a selective and sensitive analysis becomes possible.

As has been stated above, not only the radioactively labelled telluryl derivatives, but also the corresponding non-labelled telluryl compounds, if necessary obtained from enriched tellurium, can be applied for the determination of the steroid level in bodily fluids. For that purpose these compounds can be administered to patients, whereupon in a taken sample of the bodily fluid the tellurium content is determined. This determination can, if desirable, be performed with the aid of an activation analysis.

The novel compounds according to the invention are preferably represented by general formula (1) of the formula sheet, in which one of the dotted lines represents a double bond, Te represents a tellurium atom, which may be labelled radioactively $R_1$ a highly branched alkyl group $R_2$ a double-bonded oxygen atom or a hydrogen atom plus an $OR_7$ group in which $R_7$ represents a hydrogen atom, an alkanoyl group or an organic group that in a simple way can be bonded with the oxygen atom or be removed from it, $R_3$ a hydrogen atom, a hydroxyl group or a 1.5-dimethylhexyl group which may carry a methyl- or ethyl-substituent in the 4-position, $R_4$ a hydrogen atom or an acetyl- or hydroxyacetyl group or $R_3$ and $R_4$ together represent an oxygen atom, $R_5$ a methyl- or formyl group, and $R_6$ a double-bonded oxygen atom or a hydrogen atom plus a hydroxyl group or two hydrogen atoms.

The tellurium atom present in these compounds, preferably, is the $^{123m}$Te isotope, but also other Te isotopes are possible. In certain preferred compounds according to the invention, $R_3$ and $R_4$ do not simultaneously represent a hydrogen atom.

DETAILED DESCRIPTION OF THE INVENTION

Figure 1:
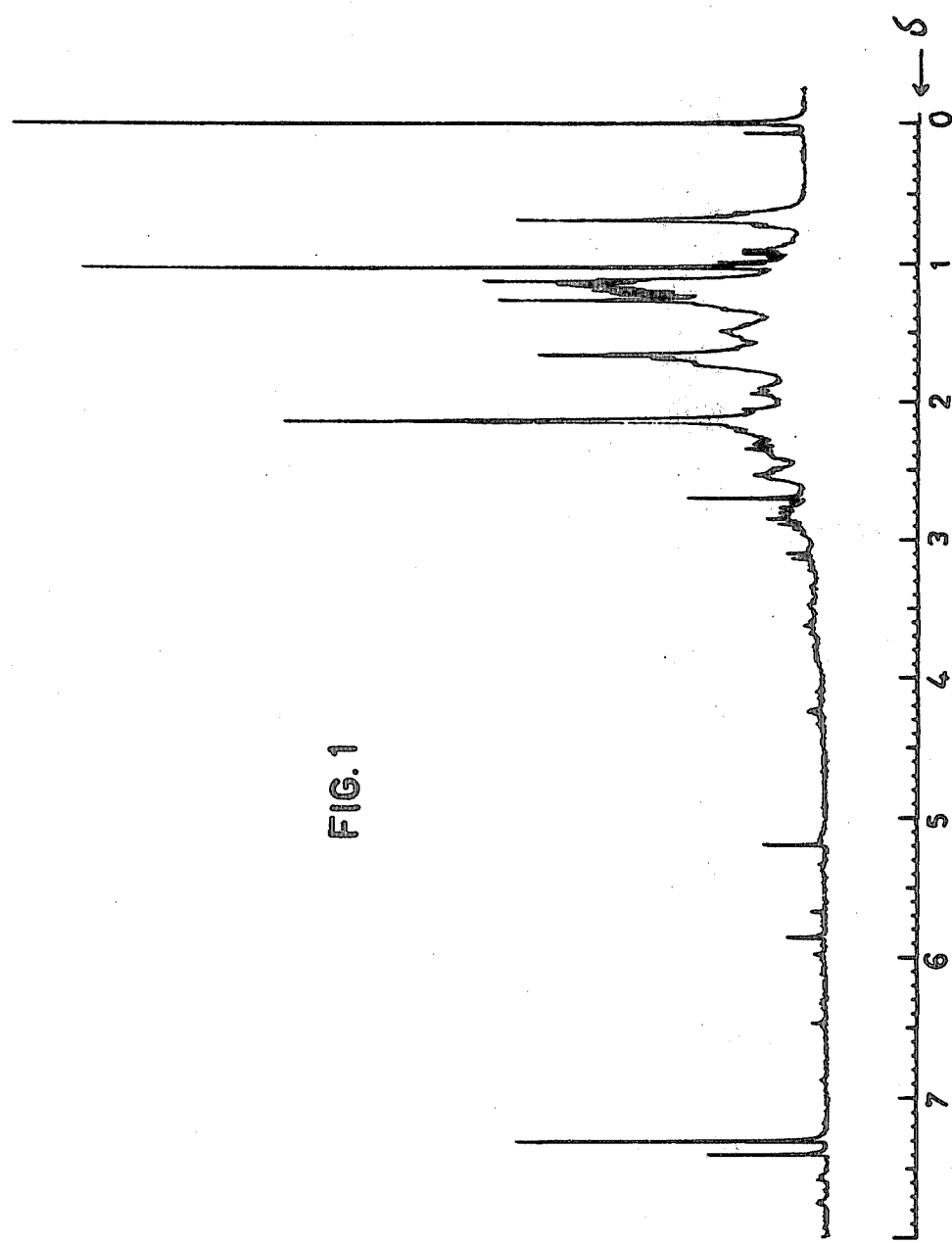
Figure 2:
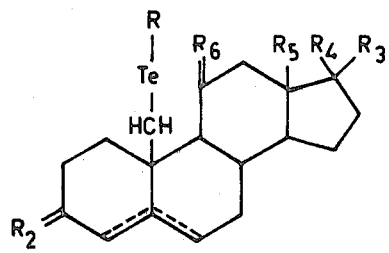
Figure 3:
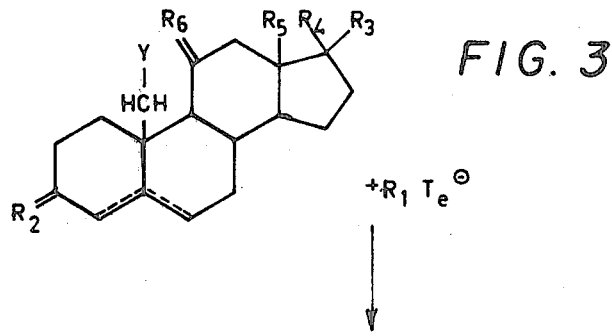
Figure 4:
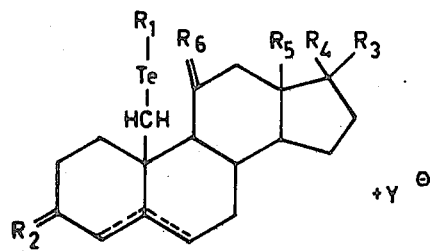
Figure 5:
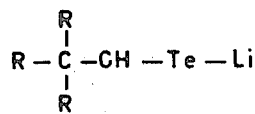

Examples of compounds into which the tellurium atom can be introduced are cholesterol, progesterone, sitosterol, pregnenolone, digoxine, etc. Also into other compounds that are applied when using scintigraphic methods the tellurium atom can be introduced advantageously instead of the customary radioisotopes so as to utilize the advantages of the invention. The protection requested also covers such compounds, their preparation and their application.

Under certain conditions the compounds according to the invention can also be applied in the form of derivatives, the hydroxyl- or oxo-groups present in the molecule being provided, according to a way known in the art, with protective groups that can easily be split off. The invention comprises also these derivatives among which are esters, labile esters, acetals, hemiacetals and the like.

It was found that the highly branched alkyl group $R_1$, which occurs in the compounds according to the invention, reduces the chemical instability caused by the presence of the tellurium atom. The explanation of this phenomenon presumably is the protective character of the highly branched alkyl group. Consequently, by a highly branched alkyl group here is understood an alkyl group that has protective character such as an ethyl group that in the $\beta$-position carries three other alkyl groups. It was found that with remarkable success the neopentyl group can be applied as highly branched alkyl group.

Neopentyl may also be named as $\beta$-dimethyl propane. Homologous compounds such as $\beta$-dimethyl butane and $\beta$-diethyl butane also show the stabilizing action; so far, these substances, have, however, been found economically less attractive.

The compounds according to the invention can be prepared according to a method known per se in the art.

For instance, the compounds can be obtained according to a method for comparable compounds as described in Applicant's Netherlands pending patent application No. 74 15526, by, starting from the steroid concerned, firstly preparing from it a derivative having general formula (2) of the formula sheet, in which in position 19 a substituent Y is present that can easily be transferred. Then this substituted steroid is reacted with a solution of an alkyl telluride, the 19-alkyl telluryl steroid desired being formed. This last nucleophile substitution reaction can be carried out by the reaction scheme of the formula sheet, in which Te, $R_1$, $R_2$, $R_3$, $R_4$, $R_5$ and $R_6$ have the meanings as defined with respect to formula (1) of the formula sheet and Y represents a group that can easily be transferred.

Easily transferable substituent Y can, for instance, be a halogen atom, in particular a bromine atom, or a methyl sulphonate group. The derivatives of steroids that in position 19 carry such an easily transferable substituent, can be obtained in ways known per se, e.g. by conversion of the corresponding 19-hydroxysteroid. Methods for the preparation of 19-hydroxysteroids are, for instance, known from J. Am. Chem. Soc. 86 (1964), 1528 and Helv. Chem. Acta 46 (1963), 1361.

Solutions of alkyl tellurides that can be used in the above-mentioned method, may, for instance, be solutions of the corresponding alkyl tellurides in a polar aprotic solvent, such as glyme (1, 2-dimethoxyethane), diglyme, triglyme, acetonitrile or tetrahydrofuran. Such solutions can be obtained according to another aspect of the invention by adding the solution of a lithium alkyl compound in a solvent customary for the purpose, such as ether or hexane, to metallic tellurium in the presence of a suitable second solvent, e.g. tetrahydrofuran or glyme. In the solution obtained a dissociation occurs, the reaction proceeding according to the scheme:

$$R_1Li + Te \rightarrow R_1TeLi \rightleftarrows R_1Te^- + Li^+$$

These compounds may also be prepared by reduction with alkali metal, for instance with sodium, of the corresponding ditellurides.

The alkyl tellurides formed are novel substances and can, as has been said, be used as intermediate products for the preparation of the alkyl telluryl steroids according to the invention. The protection requested, consequently includes these novel alkyl telluryl compounds, in particular the lithium alkyl tellurides, their solutions and their preparation.

It may be desirable or necessary, when preparing 19-telluryl derivatives, having formula (1) of the formula sheet, in which hydroxyl-, keto- and/or oxogroups are present, to protect these groups, e.g. by acetylating or benzoylating them or forming acetal. These protective group(s) may, during or after the reaction with the alkyl telluride, if desirable, be removed again. It is also possible, however, as has been stated before, to maintain this protective group in the 19-telluryl steroid.

The telluryl derivatives, having general formula (1) of the formula sheet in which $R_2$ represents an oxo-group can also be obtained by at first preparing, according to the general method as described previously, the corresponding 19-alkyl telluryl steroid, in which $R_2$ represents a hydroxyl group and then to subject this intermediate product to a mild oxidation. A suitable oxidizing agent for this purpose is, for instance, cyclohexanone in combination with aluminum isopropylate, but also other mild oxidation methods known in the art for such conversions can be applied.

The invention, furthermore, relates to diagnostic preparations based on the compounds according to the invention.

These preparations can be prepared by bringing the tellurium derivatives according to the invention in a form of application appropriate to diagnostic purposes.

This bringing in a form of application appropriate to diagnostic purposes can, for instance, take place by mixing the concerned telluryl derivative with a carrier suitable for the purpose. The preparations thus obtained can be administered to the individuals under investigation whereupon with the equipment customary for that purpose a picture can be obtained of the organs to be examined. The invention also includes the taking of such pictures for diagnostic purposes.

The diagnostic preparations according to the invention can, as stated before, also be used for diagnostic determination methods in vitro, such as for radio-immunological determinations in bodily fluids as blood and urine.

MODE OF OPERATION OF THE INVENTION

The invention will now further be elucidated with reference to the following examples:

EXAMPLE I (a). Preparation of lithium neopentyl telluride (millimol scale)

In a dry argon atmosphere a solution of neopentyl lithium in ether was added dropwisely to 140 mg of powdered metallic tellurium and 1 ml of tetrahydrofuran until the initially dark red colour had disappeared. The temperature in the reaction vessel was kept between −10° and 0° C.

(b). Preparation of lithium neopentyl telluride (50 micromol scale)

In a dry, oxygenfree argon atmosphere a solution of neopentyl lithium in hexane was added dropwisely to 6 mg of powdered metallic tellurium and 0.5 ml of tetrahydrofuran until all the tellurium had been dissolved. The temperature in the reaction vessel was kept between −15° and 0° C. while the neopentyl lithium was added.

In a corresponding way also the radioactively labelled compounds have been prepared.

EXAMPLE II

Preparation of 19-neopentyl telluryl progesterone

The solution of lithium neopentyl telluride, prepared according to Example Ib, was brought to ambient temperature and kept at that temperature for approximately half an hour. Next the volatile solvents were removed in vacuum, whereupon 21 mg of 19-bromo progesterone in 0.5 ml of diglyme were added. After standing for 1 day at ambient temperature 0.5 ml of a 5% solution of trifluoro acetic acid in tetrahydrofuran was added to the reaction mixture. Then the reaction mixture was evaporated as well as possible, the temperature being kept below 50° C. To the rough reaction product were added 1.5 ml of water; the water layer removed, whereupon another 3 times it was washed with 1.5 ml of water. The product thus obtained was dried in vacuum, whereupon it was taken up in 1 ml of dichloromethane. With this dichloromethane solution a purification was carried out by applying high pressure column chromatography, whereby 6 mg of 19-neopentyl telluryl progesterone were obtained. The NMR-spectrum of this product recorded in $CDCl_3$ is shown in FIG. 1. The mass spectrum too confirmed the structure. The NMR spectrum in $CDCl_3$ showed characteristic peaks at 0.68 ppm singlet, 18-$CH_3$); 1.02 ppm (singlet, $C(CH_3)_3$); 2.12 ppm (singlet, 17 β $COCH_3$); 2.53 ppm (triplet, 17 αH); 2.69 ppm (singlet, $TeCH_2 C(CH_3)_3$); 2.86 and 3.11 ppm (AB, 19-$CH_2Te$); 5.83 (singlet, 4-CH). All ppm values are relative in respect to tetramethylsilane (TMS) as an internal standard.

The mass spectrum showed characteristic peaks at: $m/e$ 514($M^+$ = molecule ion $^{130}Te$); $m/e$ 443($M^+$-neopentyl group); $m/e$ 400(443-acetyl group); $m/e$ 313($M^+$-$TeCH_2C(CH_3)_3$).

EXAMPLE III

Preparation of 19-neopentyl telluryl cholesteryl acetate

Such an amount of sulphuric acid in triglyme was added to the solution of lithium neopentyl telluride, prepared according to Example Ia, that the excess of base was just neutralized. Next the volatile solvents were removed in vacuum, whereupon 420 mg of 19-bromo-cholesteryl acetate in 5 ml of triglyme were added. The reaction mixture was brought to ambient temperature and kept at this temperature for 2 hours. After adding 260 mg of ammonium sulphate in 1 ml of water the solution was evaporated as much as possible (temperature not higher than 50° C.), whereupon 40 ml of water were added. The water layer was removed and the crude product washed another 2 times with 20 ml of water. After drying the product was dissolved in an organic solvent and purified by means of column chromatography. 280 mg of pure 19-neopentyl telluryl cholesteryl acetate were obtained. The structure was confirmed by means of NMR- and mass-spectrometry.

In a corresponding way radioactively labelled compounds have been prepared too.

EXAMPLE IV

Preparation of 19-neopentyl telluryl cholesterol

Under oxygen free conditions 1 ml of a 0.5 N sodium methanolate solution in methanol and some drops of water were added to a solution of 200 mg of 19-neopentyl telluryl cholesteryl acetate in 5 ml of triglyme. After standing for 2 hours at ambient temperature 200 mg of ammonium sulphate in 1 ml of water were added and then evaporated as much as possible, whereupon 40 ml of water were added. The water layer was removed and the product washed another 2 times with 20 ml of water. After drying the product was dissolved and purified by means of column chromatography, whereupon 160 mg of pure 19-neopentyl telluryl cholesterol were obtained. The structure was confirmed by means of NMR- and mass-spectrometry.

In a corresponding way radioactively labelled compounds have been prepared too.

EXAMPLE V

Preparation of 19-neopentyl telluryl sitosteryl acetate and of 19-neopentyl telluryl-sitosterol In an analogous way as described in Example III a solution of 19-neopentyl telluryl sitosteryl acetate was obtained, starting from 455 mg of 19-bromo-sitosteryl acetate. 0.2 mg was taken from this solution. The former was worked up in the customary way, 10 mg of pure 19-neopentyl telluryl-sitosteryl acetate being obtained. The structure was confirmed by means of NMR- and mass-spectrometry. 1 ml of 0.5 N sodium methanolate in methanol and some drops of water were added to the remainder of the above solution. After standing for two hours at ambient temperature it was worked up in the customary way. 290 mg of pure 19-neopentyl telluryl sitosterol were obtained. The structure was confirmed by means of NMR- and mass-spectrometry.

In a corresponding way radioactively labelled compounds have been prepared too.

EXAMPLE VI

Preparation of 19-neopentyl telluryl-pregnenolon acetate and of 19-neopentyl telluryl-pregnenolon In a way analogous to that described in Example III a solution of 19-neopentyl telluryl-pregnenolon acetate was obtained by starting from 62.4 mg of metallic tellurium and 169 mg of 19 bromopregnenolon acetate. 0.3 ml was taken from this solution and was worked up in the customary way. 6 mg of pure 19-neopentyl telluryl-pregnenolon acetate were obtained. The structure was confirmed by means of NMR- and mass-spectrometry.

1 ml of 0.5 N sodium methanolate in methanol and some drops of water were added to the remainder of the above solution. After standing for 4 hours at ambient temperature it was worked up in the customary way. 85 mg of pure 19-neopentyl telluryl-pregnenolon were obtained. The structure was confirmed by means of NMR- and mass spectrometry. In a corresponding way radioactively labelled compounds have been prepared too.

EXAMPLE VII

Preparation of 19-neopentyl telluryl—$^{123m}$Te-progesteron

Completely analogous to the method of preparation as described in Example II 19-neopentyl telluryl - $^{123m}$Te-progesteron was prepared starting from 1 millicurie of $^{123m}$Te in 6 mg of tellurium. The identity of this end product was confirmed by the identical behaviour of this compound when purified according to the high-pressure-column-chromatographic method.

I claim:

1. Telluryl derivatives of the formula

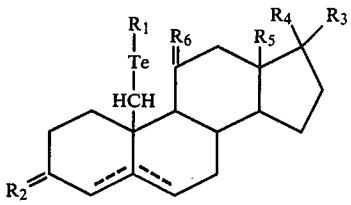

in which one of the dotted lines represents a double bond, Te is selected from the group consisting of a radioactively labelled tellurium isotope and a non-labelled tellurium atom, $R_1$ is ethyl containing in the $\beta$-position 2 to 3 alkyls of 1 to 2 carbon atoms each, $R_2$ is selected from the group consisting of a double-bonded oxygen atom and a hydrogen atom plus an $OR_7$ group, in which $R_7$ is selected from the group consisting of a hydrogen atom, an alkanoyl group and an organic group that is easily removed from the oxygen atom, $R_3$ is selected from the group consisting of a hydrogen atom, a hydroxyl group and 1,5-dimethyl hexyl, optionally containing a member selected from the group consisting of methyl, and ethyl in the 4-position, $R_4$ is selected from the group consisting of a hydrogen atom, an acetyl group and a hydroxyacetal group or $R_3$ and $R_4$ are together an oxygen atom, $R_5$ is selected from the group consisting of a methyl and a formyl group, and $R_6$ is selected from the group consisting of a double-bonded oxygen atom, a hydrogen atom plus a hydroxyl group and two hydrogen atoms.

2. The radioactively labelled telluryl derivatives of steroids of claim 1, in which Te is tellurium isotope $^{123m}$Te and $R_1$, $R_2$, $R_3$, $R_4$, $R_5$ and $R_6$ have the meanings indicated in claim 3.

3. The telluryl derivatives of steroids of claim 1, in which Te is selected from the group consisting of a radioactively labelled tellurium atom and a non-labelled tellurium atom and $R_1$, $R_2$, $R_3$, $R_4$, $R_5$ and $R_6$ have the meanings as indicated in claim 3, provided that $R_3$ and $R_4$ are not both hydrogen atoms.

4. The compounds of claim 1 in which $R_1$ is an ethyl group that in the $\beta$-position is substituted by three alkyl groups.

5. The compounds of claim 4, in which $R_1$ is a neopentyl group.

6. A member selected from the group consisting of 19-neopentyl telluryl cholesterol and the $^{123m}$Te derivative of it.

7. A member selected from the group consisting of 19-neopentyl telluryl cholesteryl acetate and the $^{123m}$Te derivative of it.

8. A member selected from the group consisting of 19-neopentyl telluryl progesteron and the $^{123m}$Te derivative of it.

9. A member selected from the group consisting of 19-neopentyl telluryl sitosterol and the $^{123m}$Te derivative of it.

10. A member selected from the group consisting of 19-neopentyl telluryl sitosteryl acetate and the $^{123m}$Te derivative of it.

11. A member selected from the group consisting of 19-neopentyl telluryl pregnenolon and the $^{123m}$Te derivative of it.

12. A member selected from the group consisting of 19-neopentyl telluryl pregnenolon acetate and the 123mTe derivative of it.

13. A method for the preparation of the stable telluryl derivatives of steroids of claim 1, wherein a compound of the formula (2)

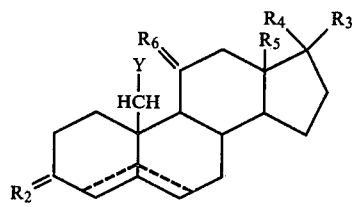

in which $R_2$, $R_3$, $R_4$, $R_5$ and $R_6$ have the meanings indicated in claim 3 and Y is an easily transferable group selected from the group consisting of halogen and sulfonates, is reacted with a solution of an alkyl telluride, said stable telluryl derivative being isolable from the reaction mixture.

14. The method of claim 13, wherein the compound of formula (2) is reacted with the solution of an alkyl telluride in a polar aprotic solvent.

15. The method of claim 13, wherein Y is a bromine atom.

16. The method of claim 14, wherein Y is a bromine atom.

17. A diagnostic preparation to be used for diagnostic investigation into abnormalities of internal organs comprising a liquid or solid carrier for the acceptable body and an effective amount of a radioactively labelled telluryl derivative of claim 1.

18. A method for the diagnostic determination of steroids in bodily fluids, wherein use is made of a telluryl derivative of claim 1.

* * * * *